United States Patent [19]
Rathfelder et al.

[11] Patent Number: 5,821,376
[45] Date of Patent: Oct. 13, 1998

[54] PROCESS FOR THE PREPARATION OF A DOP-CONTAINING MIXTURE

[75] Inventors: Paul Rathfelder, Böblingen; Horst Rieckert, Calw; Jörg Dietrich, Leinfelden-Echterdingen, all of Germany

[73] Assignee: Schill & Seilacher GmbH & Co., Germany

[21] Appl. No.: 945,432

[22] PCT Filed: Jun. 21, 1996

[86] PCT No.: PCT/EP96/02715
§ 371 Date: Oct. 24, 1997
§ 102(e) Date: Oct. 24, 1997

[87] PCT Pub. No.: WO97/00878
PCT Pub. Date: Jan. 9, 1997

[30] Foreign Application Priority Data

Jun. 23, 1995 [DE] Germany .................. 195 22 876.6

[51] Int. Cl.⁶ .............................. C07F 9/6574; C07F 9/30
[52] U.S. Cl. ................................. 558/82; 562/23
[58] Field of Search ................... 558/82; 562/23

[56] References Cited

U.S. PATENT DOCUMENTS

| | | | |
|---|---|---|---|
| 3,702,878 | 11/1972 | Saito | 260/936 |
| 5,391,798 | 2/1995 | Kleiner | 558/82 |
| 5,481,017 | 1/1996 | Kleiner | 558/82 |

FOREIGN PATENT DOCUMENTS

| | | | |
|---|---|---|---|
| 0582957 | 2/1994 | European Pat. Off. | C07F 9/6571 |
| 0632050 | 1/1995 | European Pat. Off. | C07F 9/6571 |

OTHER PUBLICATIONS

Haruna et al, "Preparation of Novel Cyclic Phosphonites" Chemical Abstracts, vol. 121, No. 21, 21 Nov. 1994, Abstract No. 246037.

*Primary Examiner*—Michael G. Ambrose
*Attorney, Agent, or Firm*—Hayes, Soloway, Hennessey, Grossman & Hage, P.C.

[57] ABSTRACT

The invention relates to a process for the preparation of 2'-hydroxydiphenyl-2-phosphinic acid in the form of a commercial mixture with 6-hydroxy-(6H)-dibenzo-(c,e)(1,2)-oxaphosphorine, the process being carried out on a commercial scale, more simply and more cheaply than previously, as a one-pot reaction without isolating intermediate products and avoiding a distillation step, with said process comprising the steps:

(a) o-phenylphenol is added to a mixture of $PCl_3$ and a Lewis acid as a catalyst while simultaneously heating the reaction mixture, and the reaction mixture is then fluxed;

(b) the resulting reaction mixture is allowed to cool and, stirring continuously, is hydrolysed, being mixed first with water and then with a low alkanol;

(c) next, the product is crystallised during further stirring, and (d) the crystalline product obtained is sucked off, washed and dried. Furthermore, the invention relates to a commercial mixture thus prepared to produce copolycondensable flameproofing agents for polyester fibers by directly reacting the mixture with itaconic acid or itaconic acid compounds, optionally together with one or more diols.

21 Claims, No Drawings

PROCESS FOR THE PREPARATION OF A DOP-CONTAINING MIXTURE

This application was filed under 35 U.S.C. 371 and is the National Stage of International Application No. PCT/EP96/02715, filed Jun. 21, 1996.

The tautomeric compounds (6H)-dibenzo-(c,e)(1,2)-oxaphosphorin-6-one (=9,10-dihydro-9-oxa-10-phosphaphenanthrene-10-oxide), usually referred to as "DOP" in the field, and 6-hydroxy-(6H)-dibenzo-(c,e)(1,2)-oxaphosphorine are known compounds, the reaction products of which with itaconic acid, itaconic acid ester or itaconic acid anhydride are widely used as copolycondensable flameproofing agents for polyester fibres. Copolycondensable flameproofing agents for polyester fibres are incorporated directly into the polyester chain during the polymerisation of the polyester and thereby become an integral constituent of the polyester chain. The flameproofing agents fixedly incorporated into the polyester fibres are by nature far superior to those flameproofing agents with which polyester fibres are subsequently finished. The preparation of the said DOP/itaconic acid derivatives and the use thereof is described in German patent specification no. 26 46 218, for example.

German patent no. 20 34 887 discloses a process for the preparation of DOP and the preparation of 2'-hydroxydiphenyl-2-phosphinic acid, a hydrolysis product of DOP, wherein o-phenylphenol is reacted under reflux with phosphorus trichloride in the presence of a Lewis acid as a catalyst, with the release of hydrogen chloride, and the resulting reaction mixtures are hydrolysed, after which crystalline products are ultimately obtained. However, none of the modifications of the process disclosed in the named patent was satisfactory for the preparation of DOP on a commercial scale, in particular for reasons of safety in the workplace, environmental protection and the cost of the apparatus needed to carry out the process.

In a modification of the known process (example 1), phosphorus trichloride and o-phenylphenol are gradually heated to 140° C. in a first step. After the release of hydrogen chloride is complete, zinc chloride is added as a catalyst, and one gradually heats to 210° C. in a second step. The reaction product must then be high-vacuum distilled (195° C., 20 torr) in a third step. Therefore, for production on a commercial scale, the entire production plant must meet the prescribed safety requirements for high-vacuum operation.

In another modification of the known process (examples 2 and 3), the first step of the process is carried out as a one-pot reaction; in the second step, however, an excess of phosphorus trichloride must then subsequently be added over a period of 15 hours, which is associated with considerable safety-related expenditure on account of the harmfulness of this chemical. After that, the mixture must be heated to 200° C. to 230° C. and then be high-vacuum distilled.

Hydrolysis of the initially formed 6-chloro-(6H)-dibenzo-(c,e)(1,2)-oxaphosphorine is carried out by the known method either by pouring the oily residue from high-vacuum distillation directly onto ice or into a sodium carbonate solution, to which activated carbon has been added. Both hydrolysis variations are unsatisfactory, with respect to both the yield and the necessary finishing steps (recrystallisation, filtration).

European patent application EP-A-0 582 957 discloses a process for the preparation of 6-chloro-(6H)-dibenzo-(c,e)(1,2)-oxaphosphorine, wherein o-phenylphenol and the catalyst are heated to 180° C. while being stirred. The phosphorus trichloride is then charged to the mixture at a temperature between 170° C. and 220° C. within 8 to 20 hours. The resulting crude product can be directly further processed, e.g. as a 50% solution in toluene or xylene.

However, as phosphorus trichloride is generally used in excess to optimise yields, vacuum distillation (165° C., 0.17 kPa) also has to be carried out in this known process.

The object of the invention is to improve a process for the preparation of 2'-hydroxydiphenyl-2-phosphinic acid in the form of a commercial mixture with 6-hydroxy-(6H)-dibenzo-(c,e)(1,2)-oxaphosphorine, wherein o-phenylphenol is reacted under reflux with phosphorus trichloride in the presence of a Lewis acid as a catalyst, with the release of hydrogen chloride, and the resulting reaction mixture is hydrolysed, after which the product is crystallised and then separated, in such a manner that, even on a commercial scale, it does not require a distillation step, in particular a high-vacuum distillation step, and requires little apparatus, but nevertheless produces a high yield of a crystalline product of sufficient purity.

According to the invention, this object is achieved in that, in a reactor fitted with a reflux condenser and a stirrer, a one-pot reaction is carried out without isolating intermediate products comprising the steps:

(a) a mixture of $PCl_3$ and a catalyst is formed and o-phenylphenol is added thereto while simultaneously heating the reaction mixture, and the reaction mixture is then refluxed;

(b) the resulting reaction mixture is allowed to cool and, during continuous stirring, is mixed first with water and then with a lower alkanol;

(c) next, the product is allowed to crystallise during further stirring, and (d) the crystalline product obtained is sucked off, washed and dried.

By combining said measures, the commercial mixture can, surprisingly, be prepared with a high yield and with sufficient purity for further processing, in particular direct conversion into itaconic acid derivatives for the production of copolycondensable flameproofing agents for polyester fibres, without a distillation step, without the expense associated with high-vacuum apparatus, without the necessity of heating to above 200° C. and without protective sluices for the subsequent dropwise addition of phosphorus trichloride.

Advantageous embodiments of the process according to the invention consist in that the $PCl_3$ is introduced at a temperature between 60° C. and the boiling temperature of the reaction mixture (pure phosphorus trichloride boils at 74.5° C. under normal conditions), in that the reaction mixture is heated in step (a) to a temperature between 80° C. and 160° C. and in that the reaction mixture is held under reflux for at least a further 3 hours after all the o-phenylphenol has been added.

The reaction mixture is preferably held under reflux for at least a further 3 hours at a temperature between 140° C. and 160° C. after all the o-phenylphenol has been added.

For good crystallisation of the product, it is furthermore preferable if the reaction mixture in step (b) is allowed to cool to a temperature between 30° C. and 50° C.

Zinc chloride is preferably used as a catalyst, and methanol, ethanol, n-propanol or isopropanol is preferably used as a lower alkanol.

With respect to the preferred further processing of the commercial mixture to form copolycondensable flameproofing agents for polyester fibres, it is advantageous if, in step (d), the sucked-off crystalline product is washed free of chloride with water and then dried.

Optimum yields are obtained when PCl$_3$ and o-phenylphenol are reacted together in a molar ratio of 1:1 to 1:1.5, preferably 1:1.25 to 1:1.35.

A further subject of the invention is a commercial mixture, prepared by the process according to the invention, for producing copolycondensable flameproofing agents for polyester fibres by directly reacting this mixture with itaconic acid, an itaconic acid ester or itaconic acid anhydride, optionally together with one or more diols.

The course of the reaction in the process according to the invention is explained in further detail with the aid of the reaction diagram below:

Firstly, o-phenylphenol (1) reacts with PCl$_3$, eliminating 1 mole of hydrogen chloride (HCl). The ester (2), formed as an intermediate product, cyclises with the aid of zinc chloride, used as a catalyst, to form 6-chloro-(6H)-dibenzo-(c,e)(1,2)-oxaphosphorine (3), releasing a further mole of hydrogen chloride. Hydrolysis of the dihydrophenanthrene derivative (3) initially produces 6-hydroxy-(6H)-dibenzo-(c,e)(1,2)-oxaphosphorine (4)—which is in tautomeric equilibrium with (6H)-dibenzo-(c,e)(1,2)-oxaphosphorin-6-one (4')—eliminating a third mole of hydrogen chloride. Further hydrolysis of this compound (4) or (4'), also known as "DOP", in the presence of a lower alkanol finally leads to ring fission, producing 2'-hydroxydiphenyl-2-phosphinic acid (5).

EXAMPLE 102.6 l (161.5 kg; 1176.47 moles) PCl$_3$ and 1.635 kg (12 moles) ZnCl$_2$ are introduced into a reactor, fitted with a reflux condenser and a stirrer, at a temperature of 70° C. 200 kg (1176.47 moles) o-phenylphenol are added to this mixture with the addition of heat, and the reaction mixture is refluxed. During the course of this, the reaction solution reaches a temperature of approximately 150° C. Hydrogen chloride gas is liberated and is collected in an absorber filled with water. After 5 to 6 hours, the o-phenylphenol has largely reacted, the reaction solution having gradually turned yellow.

The reaction solution is allowed to cool to 40° C. to 50° C. and 21.17 l water are then added, stirring continuously. Hydrogen chloride gas is once more released and collected in an absorber. A further 78 l water and 156 l ethanol are then added during further stirring and with the addition of heat, which ensures that a temperature of approximately 50° C. is maintained. During cooling, the product crystallises. It is filtered off via a suction filter, washed free of chloride with water and dried. A commercial mixture of 2'-hydroxydiphenyl-2-phosphinic acid and 6-hydroxy-(6H)-dibenzo-(c,e)(1,2)-oxaphosphorine is obtained in the form of a white crystalline powder. Yield: 85%.

Reaction diagram:

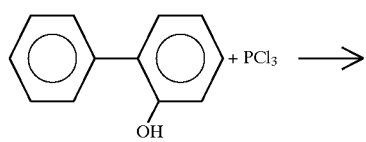

Reaction diagram:

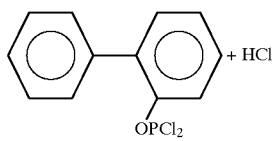

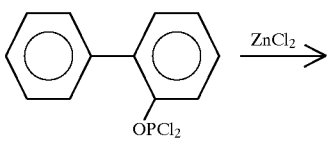

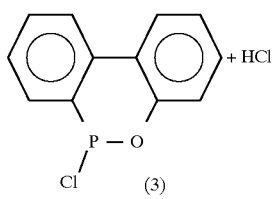

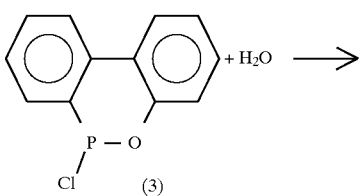

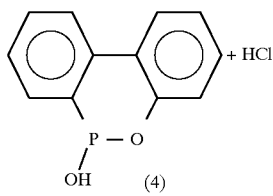

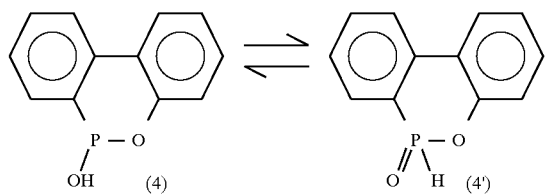

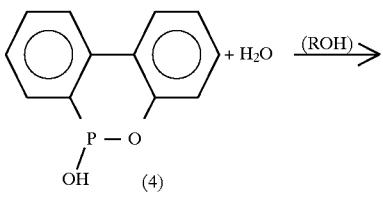

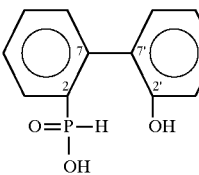

We claim:

1. A process for the preparation of 2'-hydroxydiphenyl-2-phosphinic acid in the form of a commercial mixture with 6-hydroxy-(6H)-dibenzo-(c,e) (1,2)-oxaphosphorine, wherein o-phenylphenol is reacted under reflux with phosphorus trichloride, in the presence of a Lewis acid as a catalyst, with the release of hydrogen chloride, and the resulting reaction mixture is hydrolyzed, after which the product is crystallized and then separated, characterized in that, in a reactor fitted with a reflux condenser and a stirrer, a one-pot reaction is carried out without isolating intermediate products comprising the steps:

(a) a mixture of $PCl_3$ and a catalyst is formed and o-phenylphenol is added thereto while simultaneously heating the reaction mixture, and the reaction mixture is then refluxed;

(b) the resulting reaction mixture is allowed to cool and, during continuous stirring, is mixed first with water and then with a lower alkanol;

(c) next, the product is allowed to crystallize during further stirring; and (d) the crystalline product obtained is sucked off, washed and dried.

2. The process of claim 1, wherein said $PCl_3$ is introduced at a temperature between 60° C. and the boiling temperature of the reaction mixture.

3. The process of claim 1, wherein the reaction mixture is heated in step (a) to a temperature between 80° C. and 160° C.

4. The process of claim 1, wherein the reaction mixture is held under reflux for at least a further 3 hours after all the o-phenylphenol has been added.

5. The process of claim 4, wherein the reaction mixture is held under reflux for at least a further 3 hours at a temperature between 140° C. and 160° C. after all the o-phenylphenol has been added.

6. The process of claim 1, wherein the reaction mixture in step (b) is allowed to cool to a temperature between 30° C. and 50° C.

7. The process of claim 1, wherein zinc chloride is used as a catalyst.

8. The process of claim 1, wherein methanol, ethanol, n-propanol or isopropanol is used as said lower alkanol.

9. The process of claim 1, wherein, in step (d), said sucked-off crystalline product is washed free of chloride with water and then dried.

10. The process of claim 1, wherein $PCl_3$ and o-phenylphenol are reacted together in a molar ratio of 1:1 to 1:1.5, preferably 1:1.25 to 1:1.35.

11. A process for the preparation of 2'-hydroxydiphenyl-2-phosphinic acid in the form of a commercial mixture with 6-hydroxy-(6H)-dibenzo-(c,e) (1,2)-oxaphosphorine, wherein o-phenylphenol is reacted under reflux with phosphorus trichloride, in the presence of a Lewis acid as a catalyst, with the release of hydrogen chloride, and the resulting reaction mixture is hydrolyzed, after which the product is crystallized and then separated, characterized in that, in a reactor fitted with a reflux condenser and a stirrer, a one-pot reaction is carried out without isolating intermediate products comprising the steps of:

(a) a mixture of $PCl_3$ and a catalyst is formed and o-phenylphenol is added thereto while simultaneously heating the reaction mixture, and the reaction mixture is then refluxed, with said $PCl_3$ being introduced at a temperature between 60° C. and the boiling temperature of said reaction mixture, said reaction mixture being heated to a temperature of between 80° C. and 160° C. and held under reflux for at least a further 3 hours after all the o-phenylphenol has been added;

(b) the resulting reaction mixture is allowed to cool and, during continuous stirring, is mixed first with water and then with a lower alkanol;

(c) next, the product is allowed to crystallize during further stirring; and (d) the crystalline product obtained is sucked off, washed and dried.

12. The process of claim 11, wherein the reaction mixture is held under reflux for at least a further 3 hours at a temperature between 140° C. and 160° C. after all the o-phenylphenol has been added.

13. The process of claim 11, wherein the reaction mixture in step (b) is allowed to cool to a temperature between 30° C. and 50° C.

14. The process of claim 11, wherein zinc chloride is used as a catalyst.

15. The process of claim 11, wherein methanol, ethanol, n-propanol or isopropanol is used as said lower alkanol.

16. The process of claim 11, wherein, in step (d), said sucked-off crystalline product is washed free of chloride with water and then dried.

17. The process of claim 11, wherein $PCl_3$ and o-phenylphenol are reacted together in a molar ratio of 1:1 to 1:1.5, preferably 1:1.25 to 1:1.35.

18. A process accordingly to claim 1, and including the step of: (e) reacting to crystallized product obtained in step (d) with itaconic acid, an itaconic acid ester or itaconic anhydride.

19. A process according to claim 18, wherein one or more diols is included in the reaction step (e).

20. A process accordingly to claim 11, and including the step of: (e) reacting the crystallized product obtained in step (d) with itaconic acid, and itaconic acid ester or itaconic anhydride.

21. A process according to claim 20, wherein one or more diols is included in the reaction step (e).

* * * * *